(12) United States Patent
Blackwell et al.

(10) Patent No.: US 8,268,002 B2
(45) Date of Patent: Sep. 18, 2012

(54) SLIDE-ON END CAP FOR A VERTEBRAL IMPLANT

(75) Inventors: Jonathan Blackwell, Arlington, TN (US); Thomas E. Drochner, Memphis, TN (US); Michael J. Merves, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 270 days.

(21) Appl. No.: 12/694,947

(22) Filed: Jan. 27, 2010

(65) Prior Publication Data

US 2011/0184523 A1    Jul. 28, 2011

(51) Int. Cl.
*A61F 2/44* (2006.01)
(52) U.S. Cl. .................................................. 623/17.16
(58) Field of Classification Search ..... 623/17.11–17.16
See application file for complete search history.

(56) References Cited

U.S. PATENT DOCUMENTS

| | | | | |
|---|---|---|---|---|
| 2,333,033 A | * | 10/1943 | Mraz | 606/57 |
| 4,386,603 A | * | 6/1983 | Mayfield | 606/105 |
| 5,702,453 A | * | 12/1997 | Rabbe et al. | 623/17.16 |
| 5,776,197 A | * | 7/1998 | Rabbe et al. | 623/17.15 |
| 6,193,756 B1 | * | 2/2001 | Studer et al. | 623/17.15 |
| 7,056,343 B2 | * | 6/2006 | Schafer et al. | 623/17.11 |
| 7,621,953 B2 | * | 11/2009 | Braddock et al. | 623/17.11 |
| 7,824,445 B2 | * | 11/2010 | Biro et al. | 623/17.15 |
| 7,914,581 B2 | * | 3/2011 | Dickson et al. | 623/17.16 |
| 2004/0172129 A1 | * | 9/2004 | Schafer et al. | 623/17.11 |

* cited by examiner

*Primary Examiner* — Eduardo C Robert
*Assistant Examiner* — Mary Hoffman

(57) ABSTRACT

An implant for insertion between adjacent vertebral members, comprising an implant body with a base section having positioning teeth, and an end cap adapted for positioning at a selected point on the base section via adjustment of an approach direction. The end cap comprises a seating surface adapted to contact the base section when positioned on the implant body, an end cap angulation, and positioning passages adapted to receive the positioning teeth. The implant may further comprise a locking mechanism adapted to lockingly engage the end cap and base section and prevent axial movement of the end cap. The positioning passages and positioning teeth are complementarily configured to facilitate slideably positioning the end cap on the base section. The implant body and end cap combination will impart end cap angulation to an adjacent vertebral body at the selected point when the implant is positioned in the intervertebral space.

20 Claims, 10 Drawing Sheets

SLIDE-ON END CAP FOR A VERTEBRAL IMPLANT

BACKGROUND

The present application is directed to implants, devices and methods for stabilizing vertebral members, and more particularly, to intervertebral implants, devices and methods of use in replacing an intervertebral disc, a vertebral member, or a combination of both to distract and/or stabilize the spine.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

As is known, various conditions and ailments may lead to damage of the spine, intervertebral discs and/or the vertebral members. The damage may result from a variety of causes including, but not limited to, events such as trauma, a degenerative condition, a tumor, or infection. Damage to the intervertebral discs and vertebral members can lead to pain, neurological deficit, and/or loss of motion.

Various procedures include replacing a section of or the entire vertebral member, a section of or the entire intervertebral disc, or both. One or more replacement implants may be inserted to replace the damaged vertebral members and/or discs. The implants are configured to be inserted into the intervertebral space and contact against adjacent vertebral members. The implants are intended to reduce or eliminate the pain and neurological deficit, and increase the range of motion.

The curvature of the spine and general shapes of the vertebral members may make it difficult for the implants to adequately contact the adjacent vertebral members or to position the adjacent vertebral members in a desired orientation. There is thus a need for implants or devices configurable to match the spinal anatomy for secure contact and/or desired orientation when implanted into an intervertebral space.

SUMMARY

The present application discloses implants or devices for insertion into an intervertebral space between first and second vertebral members, the implant comprising an implant body with at least one base section having positioning teeth, and an end cap adapted for selective positioning at a selected point on the base section. The end cap is selectively positioned at the selected point on the base section via adjustment of an end cap approach direction. The end cap comprises a seating surface adapted to contact the base section when the end cap is positioned on the implant body, an end cap angulation, and at least one positioning passage adapted to receive the positioning teeth. The positioning passages and positioning teeth are complementarily configured to facilitate slideably positioning the end cap on the base section. The implant body and end cap combination will impart end cap angulation to an adjacent vertebral body at the selected point when the implant is positioned in the intervertebral space. The implant may further comprise a locking mechanism adapted to lockingly engage the end cap and base section and prevent axial movement of the end cap relative to the implant base section. The implant may also comprise an end cap height measured relative to the seating surface which enables the implant to both impart end cap height and end cap angulation to the adjacent vertebral body at the selected point.

There is also provided an implant for insertion into an intervertebral space between a first and second vertebral member comprising an implant body with at least one base section having including positioning teeth, an end cap adapted for selective positioning at a selected point on the base section, and a locking mechanism comprising cooperative locking engagement between the end cap and the base section. The end cap is selectively positioned at the selected point on the base section via adjustment of an end cap approach direction. The end cap comprises a seating surface adapted to contact the base section when the end cap is positioned on the implant body, an end cap angulation, and positioning passages adapted to slideably receive aligned positioning teeth therein. The positioning passages and positioning teeth are complementarily configured to facilitate slideably positioning the end cap on the base section. The implant body and end cap combination will impart the end cap angulation to an adjacent vertebral body at the selected point when the implant is positioned in the intervertebral space. The implant locking mechanism is further adapted to prevent axial movement of the end cap relative to the implant base section. The implant may also comprise an end cap height measured relative to the seating surface which enables the implant to both impart end cap height and end cap angulation to the adjacent vertebral body at the selected point.

The various aspects of the various embodiments may be used alone or in any combination, as is desired.

DETAILED DESCRIPTION

Figure 1:
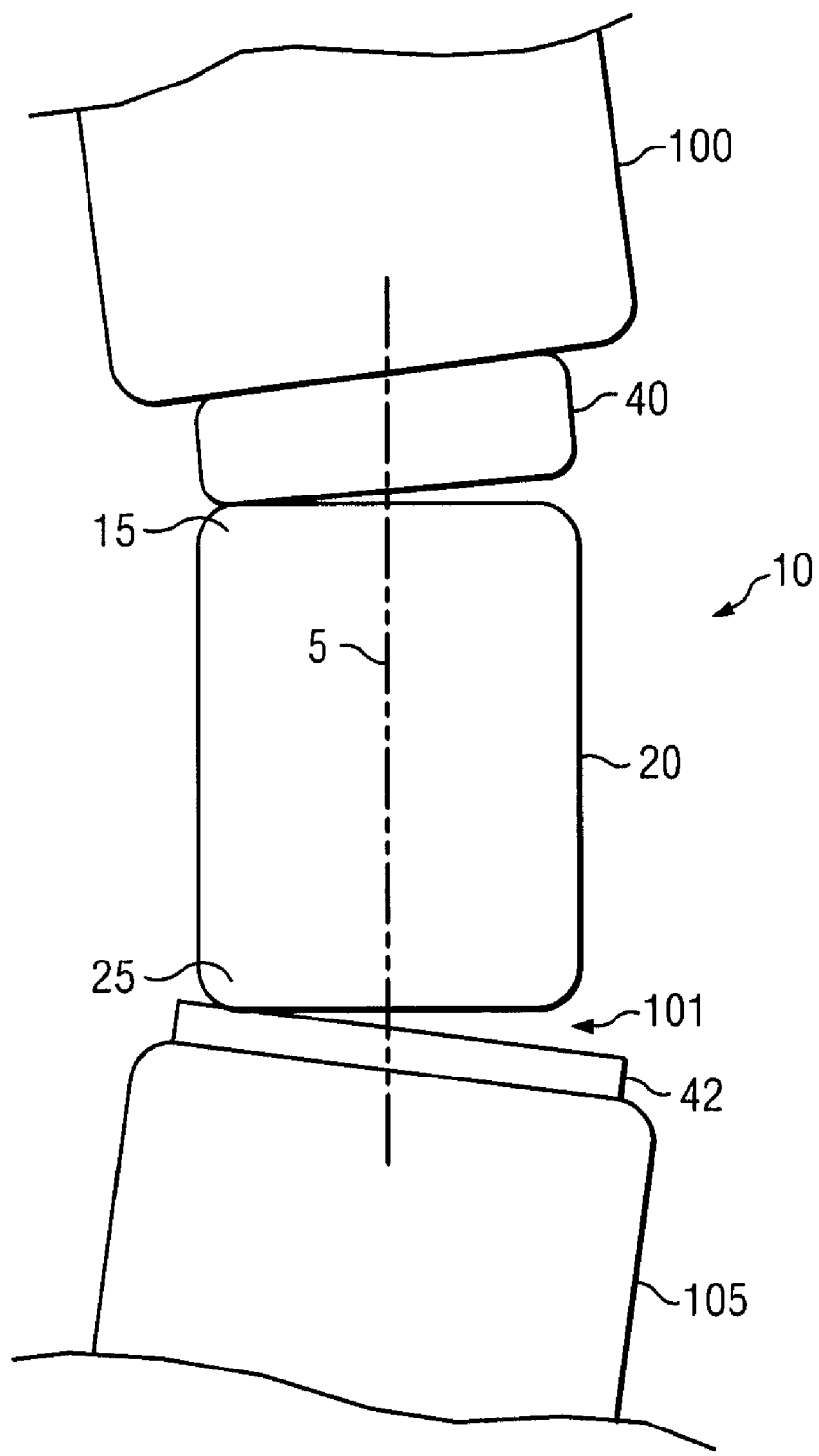
FIG. 1 is a side view of an implant positioned between vertebral members according to one embodiment.

The present application is directed to intervertebral implants for spacing apart vertebral members 100 and 105. FIG. 1 shows an implant 10 positioned within an intervertebral space 101 formed between vertebral members 100 and 105. The implant 10 includes an implant body 20 and one or more end caps 40 and 42 which are attached to the implant body 20 at a first or second implant base section 15 and 25. The one or more end caps 40 and 42 will attach or connect to the implant body 20 to impart a desired angulation θ shown in FIGS. 3 and 5, an angular orientation and/or position to the adjacent vertebral member 100 or 105. A connection or locking mechanism 50, shown in one aspect in FIGS. 2, 3 and 5, engages and locks the end cap 40 and 42 to the base section 15 and 25. This will improve the contact and stability of the intervertebral implant 10 to the adjacent vertebral members 100 and 105 and drive angular orientation for correction or improved alignment of the spine.

Figure 2:
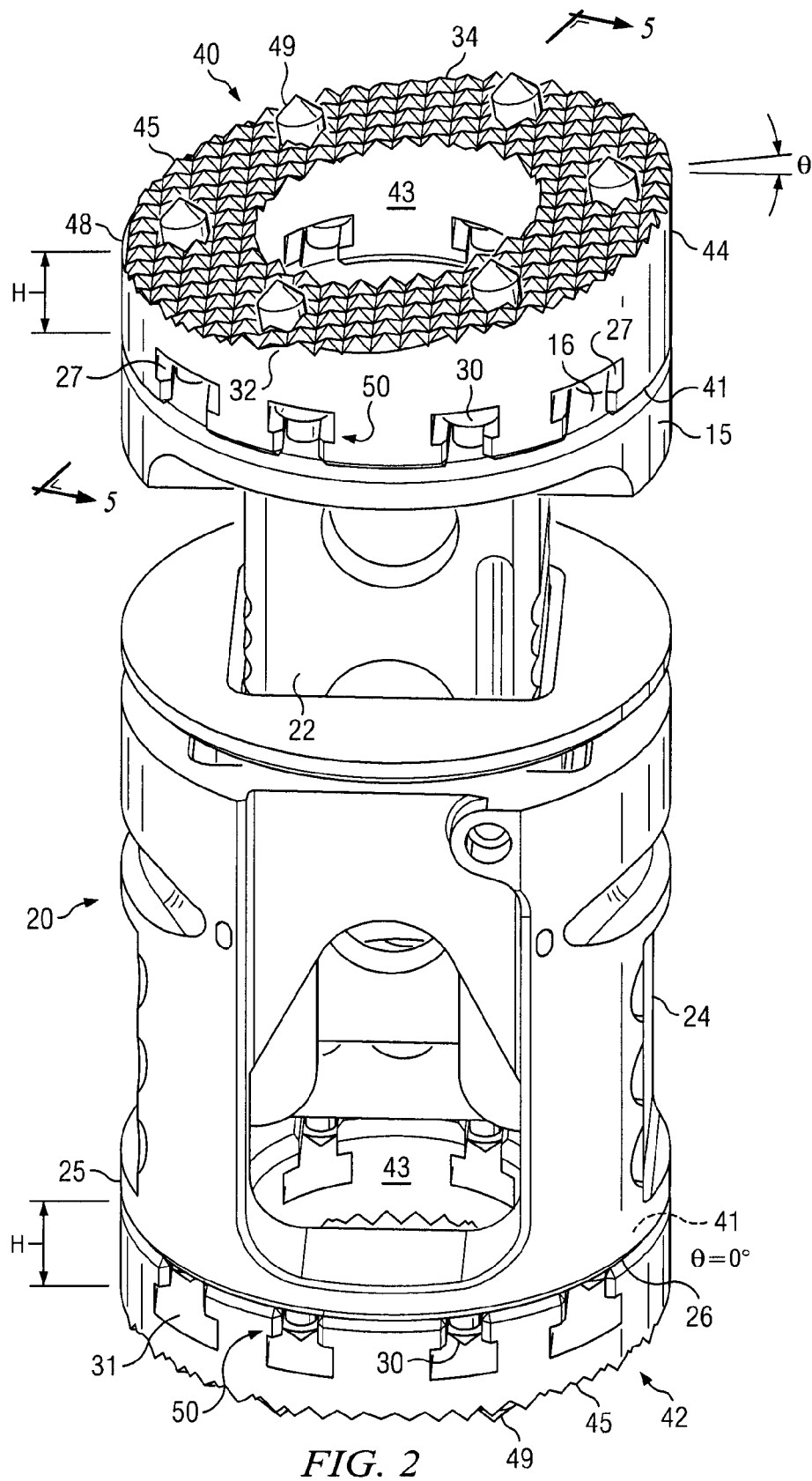
FIG. 2 is an isometric view of an implant with end caps according to one embodiment.
Figure 3:
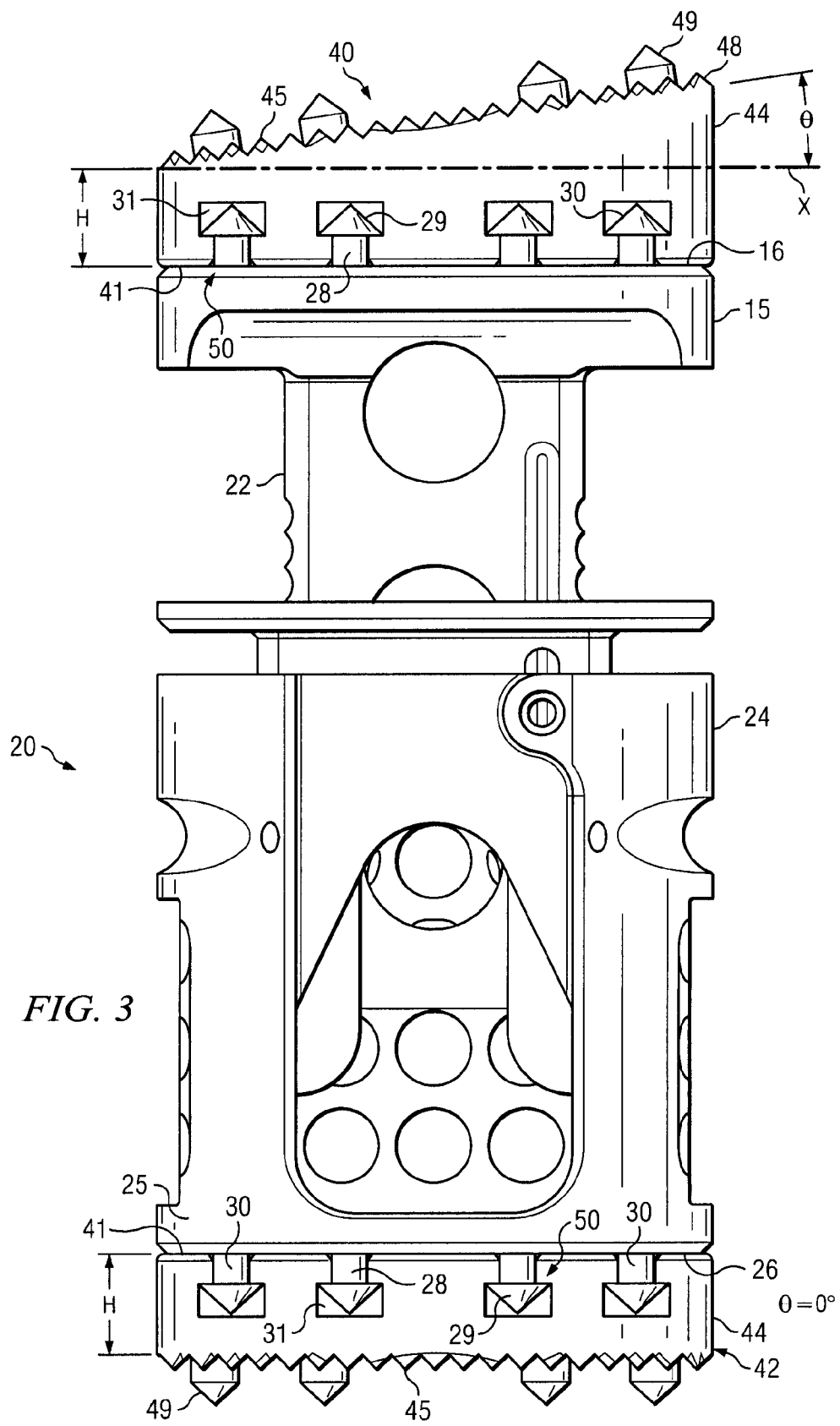
FIG. 3 is a side view of FIG. 2.
Figure 5:
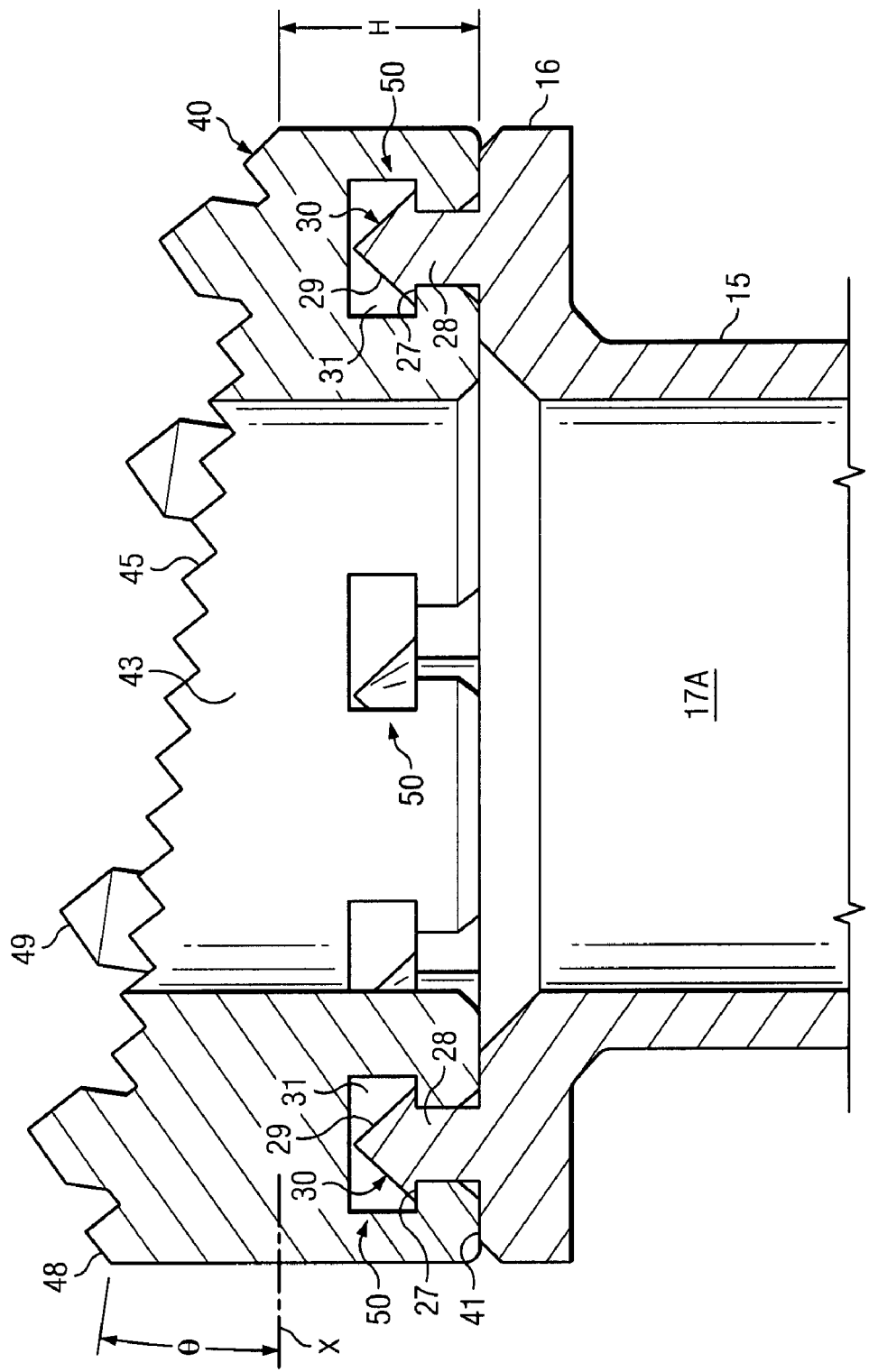
FIG. 5 is a section view along the line A-A of the implant base section and end cap of FIG. 2.

As shown in FIG. 1, the implant 10 may include first and second end caps 40 and 42 positioned at opposite ends of the implant body 20 at first and second base sections 15 and 25. The first and second end caps 40 or 42 may have the same or different configuration, height H, and/or the same or different end cap angulation θ. As shown in FIGS. 2, 3 & 5, one end cap 40 has an angulation θ, for example of 15° degrees, and a first height H, and a second end cap 42 has an angulation θ of zero degrees and a second end cap height H. Those of skill in the art will recognize that one or two end caps 40 or 42 may be used during a medical procedure with the implant 10 to impart desired or needed height H and angulation θ to adjacent vertebral members 100 or 105 and thereby correct, improve and/or stabilize the affected spinal anatomy.

Figure 4A:
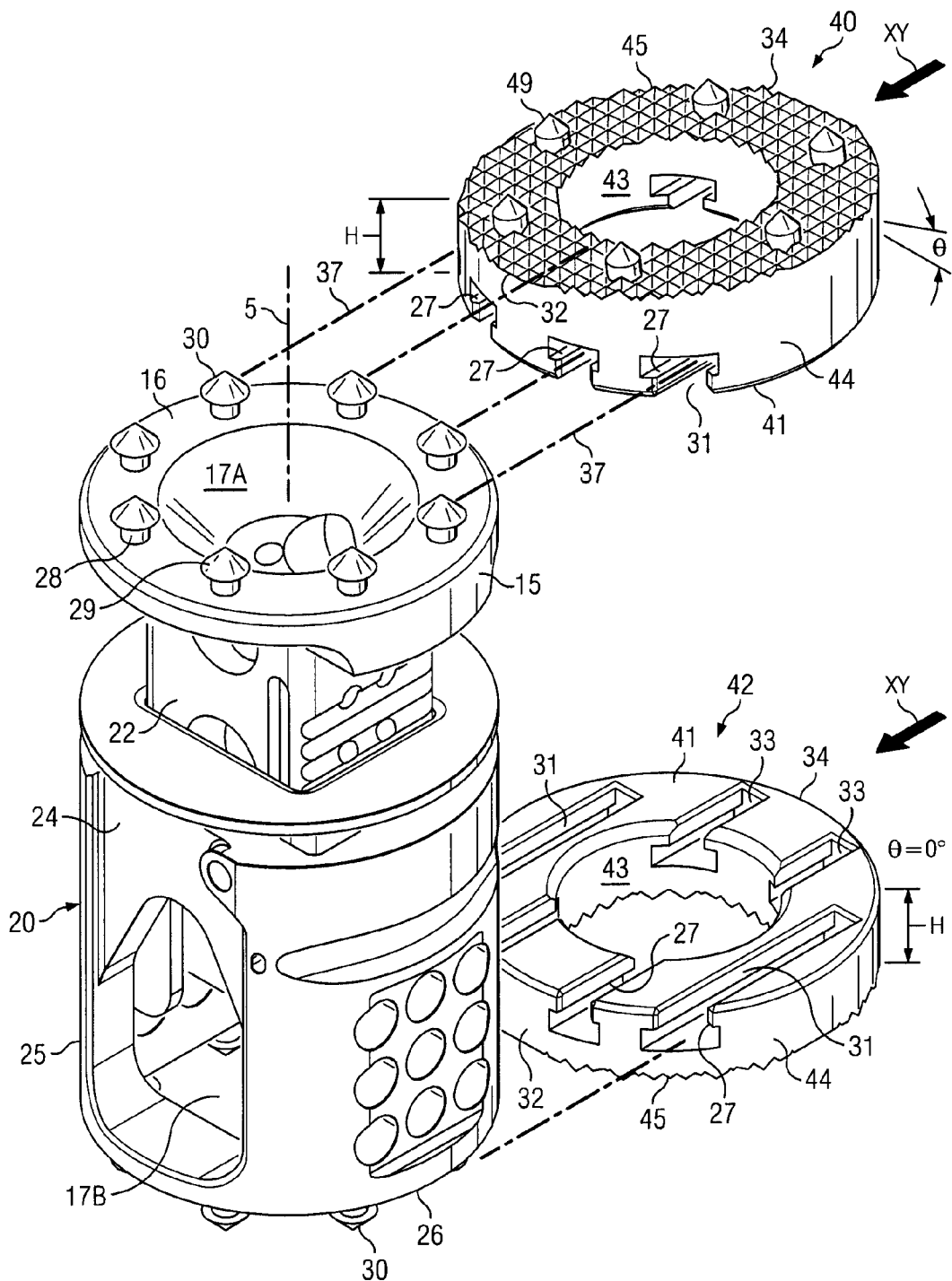
FIG. 4A is an exploded isometric view of FIG. 2.

FIGS. 2, 3 and 4A show assembled and exploded views of an implant 10 with upper and lower end caps 40 and 42 according to one embodiment. In this aspect, the implant body 20 is constructed of two implant sections 22 and 24 which are movable relative to each other so as to permit adjustment of the axial height of the implant 10. The implant body 20 includes an inner implant body 22 adapted to axially travel inside an outer implant body 24 to thereby enable selected or controlled collapse and expansion of the implant 10. The outer implant body 24 includes a hollow interior and the inner implant body 22 includes a first base section 15. The inner implant body 22 is sized to fit within and axially travel along the hollow interior of the outer implant body 24 to adjust the height of the implant body 20 along the longitudinal axis 5. Both the inner and outer implant bodies 22 and 24 may be hollow and include one or more apertures to receive bone growth material. Also, one or more apertures may extend through the body 20 walls to the hollow interior. The implant body 20 may also be constructed from a single section with a fixed height measured between the first and second base sections 15 and 25.

The implant body 20 is configured to slideably receive the end cap 40 or 42 at the first and second base sections 15 and 25, respectively, from a substantially lateral and perpendicular direction to the implant's longitudinal axis 5. The inner implant body 22 includes a first base section 15 with positioning teeth or spikes 30. The positioning teeth or spikes 30 are positioned substantially about the periphery of the first base section 15 and extend away from an exterior surface 16 of the first base section 15 in a substantially vertical or axial direction. The outer implant body 24 includes a second base section 25 with similar positioning teeth or spikes 30. The positioning teeth or spikes 30 are positioned substantially about the periphery of the second base section 25 and extend away from an exterior surface 26 of the first base section 15 in a substantially vertical or axial direction.

The implant base section 15 and 25 includes base apertures 17A and 17B, shown in FIG. 4A, adapted to receive or permit delivery of bone growth material into the implant 10 which will augment fusion in the disc space 101 once the implant is in place between the vertebral members 100 and 105. The base apertures 17A and 17B are preferably adjacent and aligned with a corresponding end cap central aperture 43. Those of skill in the art will recognize that the base aperture 17 and end cap central apertures 43 may also be non-aligned if desired or needed by a surgeon, medical procedure or clinical application.

The implant base section 15 and 25 comprises two or more positioning teeth or spikes 30 to accept and provide for slideable placement, positioning and engaging of the end cap 40 or 42 onto the implant base section 15 and 25 as shown in FIGS. 2-4A & 5. In a preferred aspect, the positioning teeth 30 are configured to be inserted into and slideably travel inside the end cap 40 or 42 via corresponding and complementary configured positioning passages or end cap slots 31. In the aspect shown in FIGS. 2-4A and 5, the positioning teeth 30 comprise a tooth head 29 and a tooth base 28 where the tooth head 29 is wider than the tooth base 28 at their junction. In the aspect shown in FIGS. 2-4A and 5, the positioning teeth 30 are shaped to resemble an arrow configuration. Those of skill in the art, will readily recognize that other positioning teeth 30 shapes or configurations may instead be used, so long as the positioning teeth 30 can enter and slideably travel within the positioning passages or end cap slots 31 to permit the end cap 40 or 42 to be slideably positioned on the exterior surface 16 or 26 of the implant base section 15 or 25.

The positioning teeth 30 enable the end cap 40 or 42 to be inserted into and slideably travel inside the end cap 40 or 42 via corresponding and complementary configured positioning passages or end cap slots 31. The positioning passages 31 are preferably end cap slots complementarily shaped and configured to permit the positioning teeth 30 to enter and slideably travel therein. The positioning teeth 30 are also adapted to interlock and engage with the corresponding and complementary positioning passages or end cap slots 31 to form an end cap locking mechanism 50, shown in FIGS. 3 & 4A. In one aspect, shown in FIGS. 2-4A and 5-7B, the positioning passages or end cap slots 31 have a substantially T-shaped aperture configuration with slot shoulder walls 27 which will interact with the underside of the positioning teeth heads 29. The positioning passages or end cap slots 31 extend from a first end 32 of the end cap 40 or 42 across and towards an opposing second end 34 of the end cap 40 or 42. The T-shaped end cap slot 31 are complementarily sized to permit the end cap teeth 30 to enter and slideably travel within the T-shaped end cap slots 31 as the end cap 40 or 42 is moved across the first or second base sections 15 or 25. The complementary positioning teeth 30 and end cap slots 31 enable the end cap 40 or 42 to be slid onto the first or second base section 15 or 25, and interact and engage the complementary positioning passages or end cap slots 31 to form the end cap locking mechanism 50, shown in FIGS. 3 & 5.

FIGS. 2, 3 and 5 show the locking mechanism 50 which in one aspect comprises positioning teeth 30 which engage and interlock with a plurality of corresponding and complementary positioning passages or end cap slots 31 to secure the end cap 40 or 42 to the first or second base sections 15 or 25. As the end cap 40 or 42 slideably travels over and across the exterior surface 16 or 26 of the implant base section 15 or 25, the positioning teeth 30 enter and engage the end cap slots 31 and thereafter slideably travel inside the end cap slots 31. The positioning teeth 30 and the end cap slots 31 have complementary shapes or configurations such that they cooperatively interact to lock or secure the end cap 40 or 42 onto the first or second base sections 15 or 25. The locking mechanism 50 permits the end cap 40 and 42 and the base section 15 and 25 to engage and interlock when the end cap 40 or 42 is slideably positioned on the base section 15 or 25. Those of skill in the art will readily recognize that other locking mechanism may be used to engage and lock the end cap 40 and 42 to the base section 15 and 25. Other sizes, shapes and configurations may also be used for the positioning teeth 30 and the positioning passages 31, as long as they have a complementary sliding configuration which permits the positioning teeth 30 to engage and interlock with the corresponding and complementary end cap slots 31 when the end cap 40 or 42 is slideably positioned on the implant base section 15 and 25. For example, such as the locking mechanism 150 shown in FIG. 8 which is discussed below.

The fit between the interlocking or engaging positioning teeth 30 and end cap slots 31 is preferably a friction fit sufficient to minimize or prevent movement between the positioning teeth 30 and end cap slots 31 once the end cap 40 or 42 is positioned at a desired end cap position on the first or second base section 15 or 25. The holding strength of the friction fit may be augmented or controlled by the addition or use of a coating substance between the end cap slots 31 and the positioning teeth 30. For example, a coating, such a silicone, may be used to increase friction between the end cap slots 31 and the positioning teeth 30. Those of skill in the art will recognize that other substances or friction control mechanism may be used to augment or control friction strength between the end cap slots 31 and the positioning teeth 30.

Additionally, the positioning teeth 30 and complementary positioning passages or end cap slots 31 cooperatively engage and interact to prevent movement or travel of the end cap 40 or 42 in an axial direction along the implant axis 5 relative to the first or second base section 15 or 25. Since the tooth head 29 is wider and larger than the tooth base 28, an attempt to move or remove the end cap 40 or 42 in an axial direction will result in the end cap slot shoulder walls 27 butting up against the underside of the tooth head 29 thereby preventing axial movement or removal of the end cap 40 or 42 from the first or second base section 15 or 25.

FIG. 4A is an exploded isometric view of FIGS. 2 and 3 showing the implant 20 and corresponding end caps 40 and 42. The end cap 40 or 42 is aligned and oriented such that the end cap's first end 32, having the open end of the positioning passages 31, will approach the positioning teeth 30 for entry into the end cap slots 31. The positioning teeth 31 extend away from the exterior surface 16 of the first base section 15 in a substantially vertical or axial direction and perpendicular to a horizontal plane containing the exterior surface 16. As a result, the implant body 20 can receive the end cap 40 or 42 at its first and second base sections 15 and 25 from an approach direction and orientation XY that is substantially parallel to a horizontal plane containing the exterior surface 16 or 26, and perpendicular to the implant's longitudinal axis 5 and positioning teeth 31. Those of skill in the art will recognize that if the positioning teeth 30 and exterior surface 16 or 26 take on other orientations, then the end cap 40 of 42 with complementary shaped end cap slots 31 will use a different and corresponding approach direction and orientation XY so that the end cap 40 or 42 can be slideably positioned on the first or second base section 15 or 25.

Once the end cap 40 or 42 is at a desired or selected approach direction and orientation XY, the end cap 40 or 42 can be positioned on the implant base section 15 or 25. The end cap 40 or 42 is moved to approach the implant base section 15 or 25 from a direction and orientation XY that is substantially perpendicular to the implant's longitudinal axis 5 and parallel to the exterior surface 16 or 26, which permits the end cap 40 or 42 to be slideably positioned on the exterior surface 16 or 26 of the implant base section 15 or 25. The complementary positioning teeth 30 and positioning passages 31 enable the end cap 40 or 42 to be slideably positioned on the implant base section 15 or 25.

As the first end 32 of the end cap 40 or 42 approaches the implant base section 15 or 25, the positioning passages or end cap slots 31 permit the positioning teeth 30 to enter the end cap slots 31, which in turn permit the end cap 40 or 42 to slideably travel over and across the exterior surface 16 or 26 of the implant base section 15 or 25. The positioning teeth 30 are configured to slideably travel inside the positioning passages or end cap slots 31 as the end cap 40 or 42 is actively moved or forced over and across the exterior surface 16 or 26. So long as the end cap 40 or 42 is actively moved or forced over and across the exterior surface 16 or 26, the positioning teeth 30 will continue to slideably travel inside the end cap slots 31 until the end cap 40 or 42 reaches a desired end cap position on the implant base section 15 or 25. The desired end cap position on the implant base section 15 or 25 can be selected by a physician or may be selected to meet, or dictated by, medical or surgical needs. The desired end cap position may be an end cap position where the end cap 40 or 42 is centered and aligned with the implant's axis 5, as shown in FIGS. 2, 3 and 5. At the desired end cap position, the positioning teeth 30 interlock and engage the plurality of complementary positioning passages or end cap slots 31 to form the end cap locking mechanism 50, discussed above, to lock the end cap 40 or 42 onto the first or second base sections 15 or 25.

The positioning teeth 30 can also slideably travel inside the end cap slots 31 until at least one positioning tooth 30 reaches and abuts up against a corresponding positioning passage wall or slot wall 33 located at or about an opposing second end 34 of the end cap 40 or 42, as shown in FIGS. 4A and 6A-7B. When one or more positioning teeth 30 reach and abut up against a positioning passage slot wall 33, the slot wall 33 will obstruct and prevent further travel of the positioning teeth 30 inside the end cap slot 31. If an attempt is made to continue to move or force the end cap 40 or 42 to travel over or across the implant base section 15 or 25, the positioning passage slot wall 33 will prevent further sliding travel of the positioning teeth 30. When at least one positioning tooth 30 reaches and abuts against a corresponding positioning passage slot wall 33, the end cap 40 or 42 has reached a final end cap position on the implant base section 15. The final end cap position may be an end cap position where the end cap 40 or 42 is centered and aligned with the implant's axis 5, as shown in FIGS. 2, 3 and 5. Alternatively, the final end cap position on the implant base section 15 or 25 may instead be selected by a physician or may be selected to meet, or dictated by, medical or surgical needs. At the final end cap position, the positioning teeth 30 engage and interlock the plurality of complementary positioning passages or end cap slots 31 to form the end cap locking mechanism 50 and lock the end cap 40 or 42 onto the first or second base sections 15 or 25. Those of skill in the art will recognize that the desired end cap position and the final end cap position may be the same position or may be different positions on the implant base section 15 or 25.

Those of skill in the art will recognize further, that in other aspects, it may be advantageous to have an end cap 40 or 42 with positioning passages or end cap slots 31 that do not have corresponding positioning passage slot walls 33. In such an aspect, as the end cap 40 or 42 is actively moved across the implant base section 15 or 25, the positioning teeth 30 will continue to slideably travel inside the end cap slots 31. If the end cap 40 or 42 continues to be slideably moved across the exterior surface 16 or 26, such that the end cap's opposing second end 34 travels past the starting point where the end cap first end 32 initially traveled over the implant base section 15 or 25, then the end cap's first end 32 will travel completely across and past the implant base section 40 or 42. And further, if the end cap 40 or 42 continues to be moved slideably across the implant base section 15 or 25, the end cap's opposing second end 34 will continue to travel across the implant base section 15 or 25 until the end cap's second end 34 too will have traveled completely across and past the implant base section 15 or 25. At this point, the end cap 40 or 42 would be separate from the implant base section 15 or 25 since it has now traveled completely across and past the implant base section 40 or 42. The final end cap position on the implant base section 15 or 25 in such an aspect will be selected by a physician or may be selected to meet, or dictated by, medical or surgical needs.

Figure 4B:
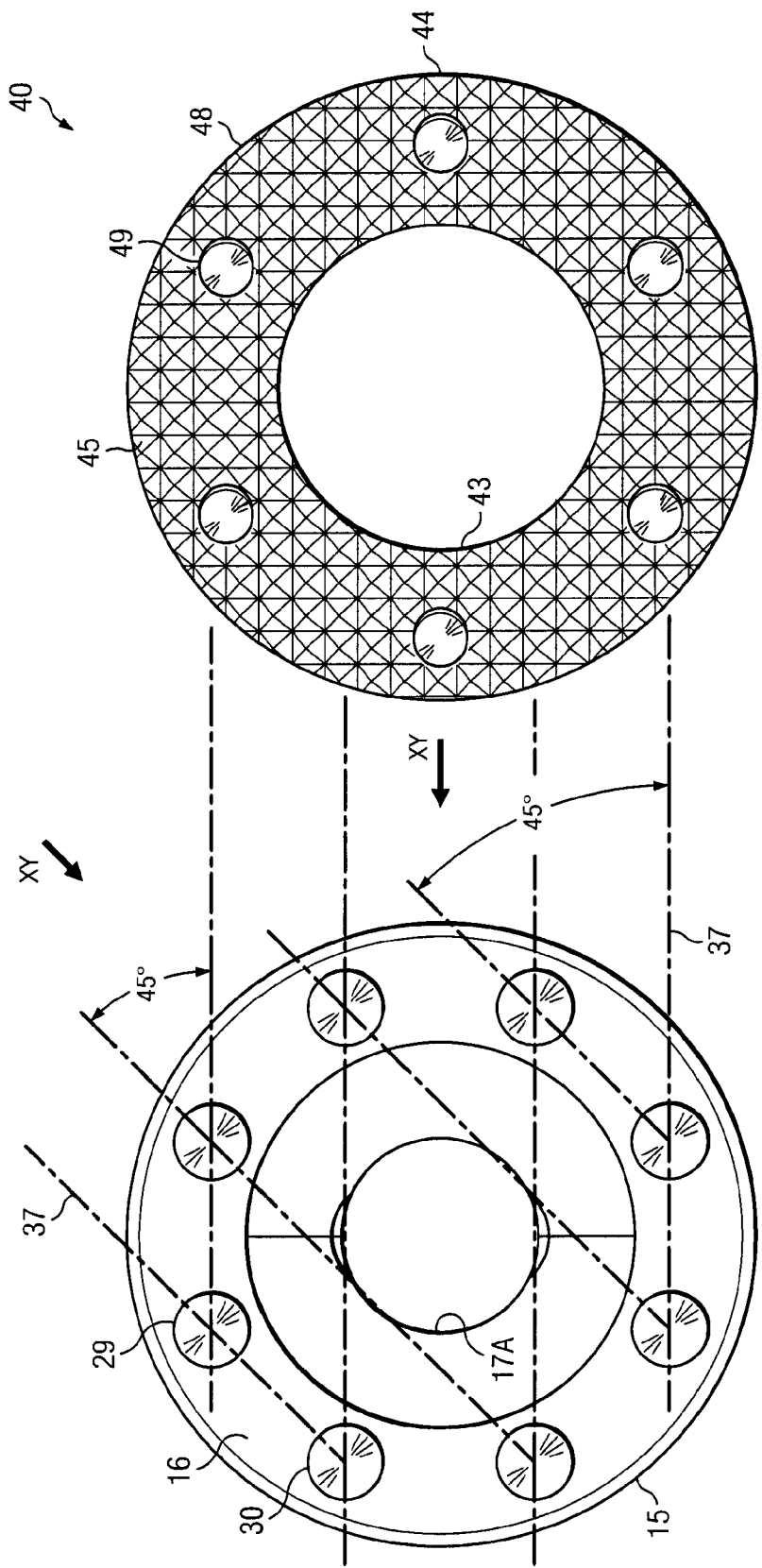
FIG. 4B is a top view of FIG. 4A.
Figure 6A:
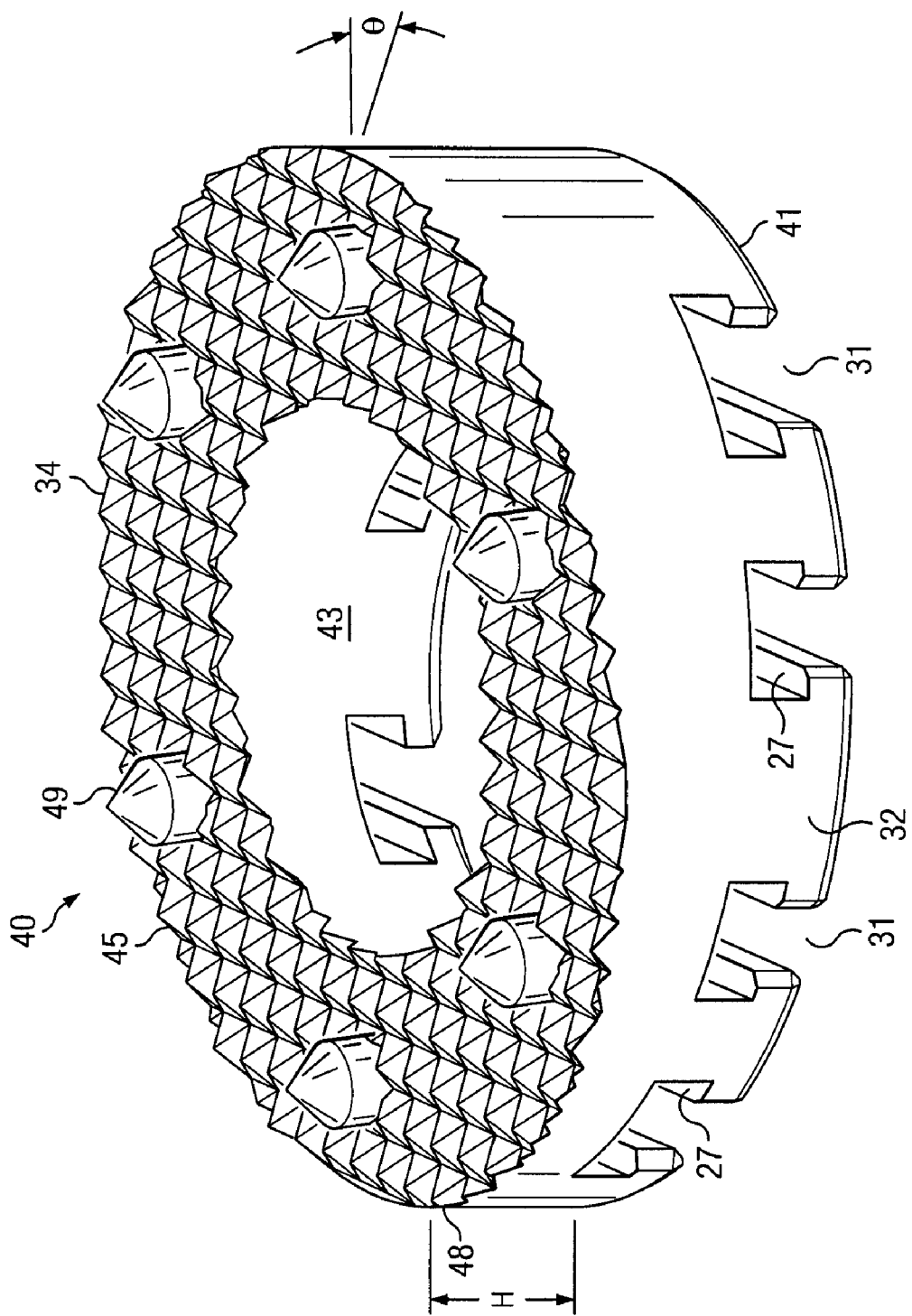
FIG. 6A is an isometric view of an end cap according to one embodiment.
Figure 6B:
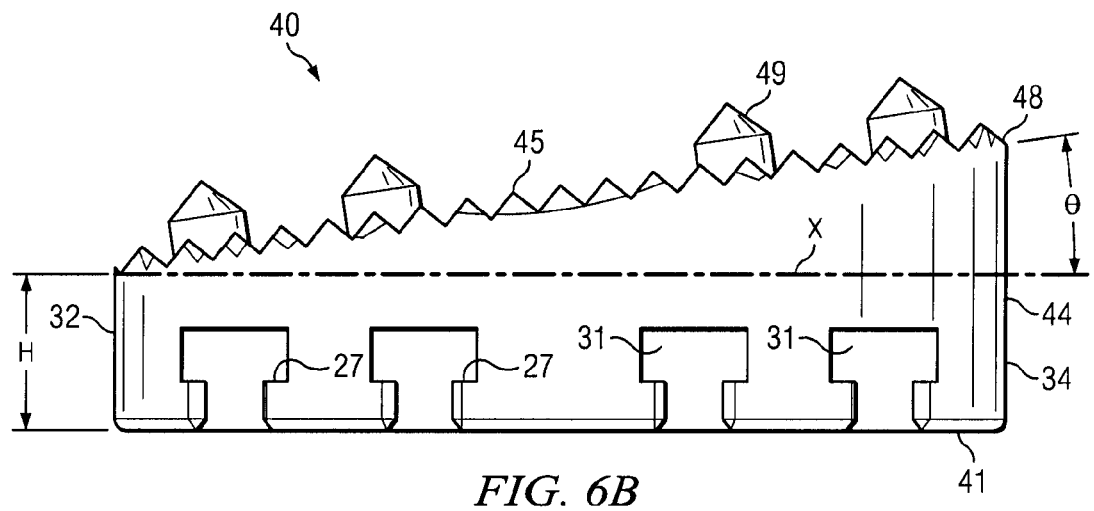
FIG. 6B is a side view of FIG. 6A.
Figure 6C:
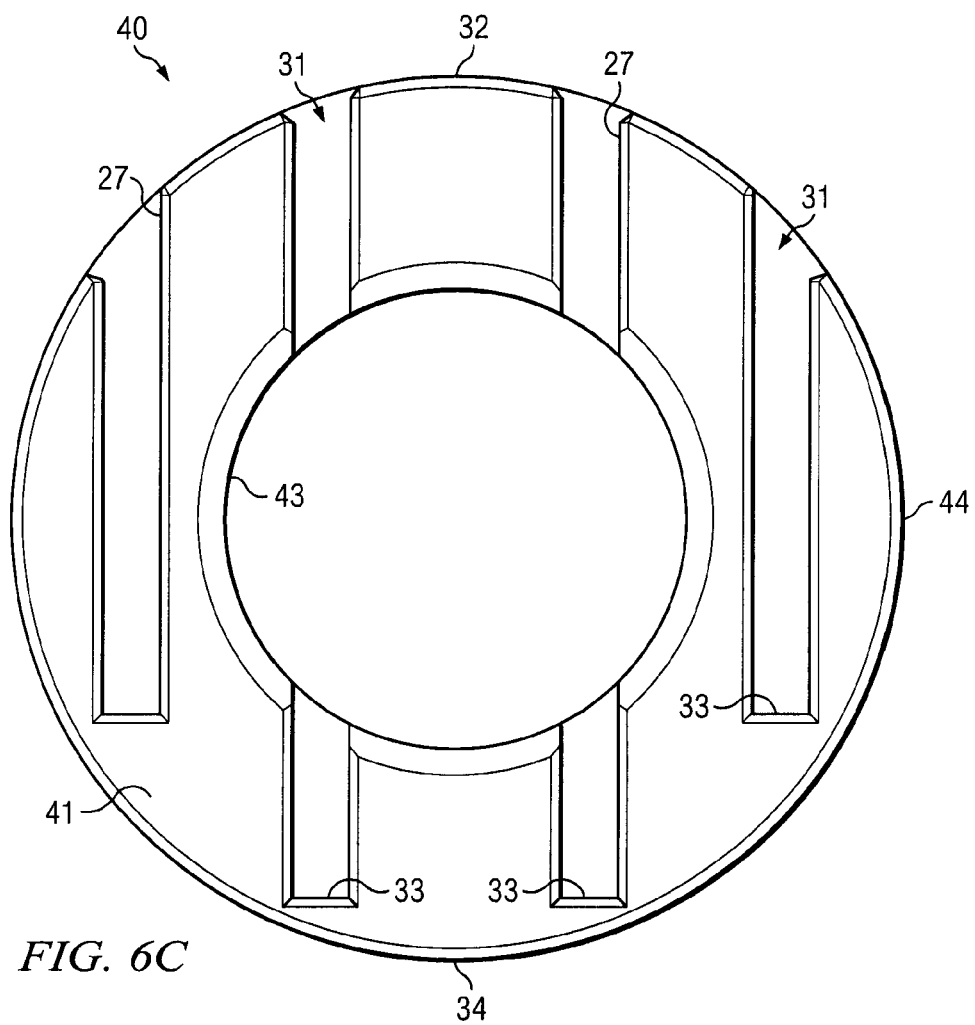
FIG. 6C is a bottom view of FIG. 6A.

FIGS. 4A and 4B shown exploded isometric and top views on an implant 20 and corresponding end caps 40 or 42 according to one aspect. FIG. 5 is a section view along the line A-A of the implant base section 15 and end cap 40 of FIG. 2. FIGS. 6A-6C are views of the end cap 40 of FIG. 4A. The implant base section 15 comprises positioning teeth 30 which will interact with the positioning passages or end cap slots 31 to interlock the end cap 40 or 42 with the implant base section 15 or 25. The positioning teeth 30 provide for stable placement and slideable positioning of the end cap 40 or 42 onto the implant base section 15 via slideable positioning with corresponding positioning passages or end cap slots 31. In one aspect, the implant base section 15 or 25 preferably has eight positioning teeth 30 to accept slideable positioning of the four slotted end cap 40 onto the implant base section 15. The positioning teeth 30 and the positioning passages or end cap slots 31 have complementary configurations which permit the positioning teeth 30 to engage and interlock with the complementary shaped end cap slots 31 when the end cap 40 or 42 is slideably positioned on the implant base section 15 and 25. The positioning teeth 30 and the positioning passages or end cap slots 31 cooperatively interact to form the locking mechanism 50 to lock and secure the end cap 40 or 42 onto the first or second base sections 15 or 25.

FIGS. 4A, 4B and 6A-7B also show that the end cap 40 comprises an annular-like shape with an exterior contact surface 48 with extending end cap teeth 45 and spikes 49, positioning passages or end cap slots 31, a seating surface 41, a substantially vertical exterior cap wall 44 and a central aperture 43. The exterior contact surface 48 and a seating surface 41 are bounded by the vertical exterior cap wall 44 and the central aperture 43. The contact surface 48 extends around the central opening 43. The central aperture 43 is preferably aligned with and the same size as the corresponding base aperture 17A or 17B. Those of skill in the art will recognize that the central aperture 43 and base aperture 17A or 17B may also be of different sizes and non-aligned if desired or needed by a surgeon, medical procedure or clinical application.

The contact surface 48 can include end cap knurls or teeth 45 and/or spikes 49 which will engage the end plates of an adjacent vertebral member 100 or 105. The end cap teeth 45 or spikes 49 may be a series of equidistantly spaced end cap teeth 45 or spikes 49 extending from the end cap exterior surface 48, as shown in FIGS. 2-7B. Those of skill in the art will recognize that the end cap teeth 45 or spikes 49 may have other arrangement and number of end cap teeth 45 and spikes 49 that may depend on the medical procedure, on clinical need, or surgeon need or selection. For example, the end cap teeth 45 could also be a series or pattern of uniform knurls or teeth 45 that cover the entire end cap exterior surface 48 and assist in providing a securing and stabilizing function of the combined end cap 40 or 42 and implant body 20 (as shown in FIG. 8) or solely large spikes 49 (not shown), so long as they assist in providing a securing and stabilizing function of the combined end cap 40 or 42 and implant body 20. Those of skill in the art will recognize that the number, size, height, shape, orientation and spacing of the end cap teeth 45 or spikes 49 may vary according to the needs of a medical procedure or clinical application.

The end cap teeth 45 and spikes 49 will come in contact with and engage the end plates of an adjacent vertebral body 100 or 105 once the combined implant body 10 and end cap 40 or 42 are positioned in an intervertebral space 101 between the vertebral members 100 and 105. The end cap teeth 45 and spikes 49 will extend from the end cap exterior surface 48 sufficiently to grip, penetrate and embed into the adjacent vertebral member 100 and 105 end plate to thereby provide implant stability in the intervertebral disc space 101 and prevent the inserted implant 10 from being ejected out of the intervertebral space 101 after implant 10 insertion. The end cap teeth 45 and spikes 49 will provide a securing and stabilizing function of the combined end cap 40 and implant body 10. The actual height of the end cap teeth 45 or spikes 49 can vary to accommodate the selection or need of a surgeon, medical procedure or clinical need. When an implant 10, with positioning base teeth 30 and one or two end caps 40 or 42, is inserted into an intervertebral space 101 and set to a desired implant height, via appropriate instruments (not shown), the protruding end cap teeth 45 and spikes 49 will grip and penetrate into the adjacent vertebral member end plate to maintain a stable implant 10 position between the adjacent vertebral members 100 and 105.

As discussed previously, the end cap 40 or 42 positioning passages or end cap slots 31 have complementary sliding configurations to the positioning teeth 30 which permit the end cap slots 31 to engage and interlock and with the plurality of corresponding and complementary shaped positioning teeth 30 when the end cap 40 or 42 is slideably positioned on the implant base section 15 and 25. The positioning passages or end cap slots 31 and positioning teeth 30 cooperatively interact to form the locking mechanism 50 to lock the end cap 40 or 42 onto the first or second base sections 15 or 25. When the end cap 40 or 42 is positioned on the implant base section 15 or 25, the positioning teeth 30 provide for a stable placement and positioning of the end cap 40 onto the implant base section 15 or 25 via complementary interaction with corresponding end cap slots 31. The positioning teeth 30, in addition to providing a mechanism to accept placement of the end cap 40 or 42 on the implant base section 15 or 25, provide a securing and stabilizing function so that the end cap 40 or 42 can be securely and slideably positioned on the implant base section 15 and 25.

The end cap 40 further comprises an angulation θ aspect and an end cap vertex height H. The end cap angulation θ and cap height H may have a range of values as may be selected or needed by a surgeon, medical procedure or clinical application. In one aspect, preferred discrete values for end cap angulation are 0°, 4°, 8° and 15° degrees measured from an angulation reference line X, shown in FIGS. 3 and 5-7B. In other embodiments, the preferred angulation θ values may be in the range of zero and thirty degrees)(0°-30°, with a preferred range of between zero and fifteen degrees)(0°-15°. In one aspect, the cap height H may have preferred values in 1.0 mm or 0.5 mm increments measured from the end cap seating surface 41. The angulation reference line X is preferably at the cap height H value as shown in FIGS. 3 and 5-7B. The end cap's angulation θ is a measure of the inclination of the exterior contact surface 48 relative to the angulation reference line X. Insertion of an implant 10 with an end cap 40 having an angulation θ aspect enables the end cap 40 to impart a desired or selected angulation θ to an adjacent vertebral member 100 or 105. In this manner, selective angulation θ can be imparted to the adjacent vertebral body 100 or 105 and thereby assist in the correction and/or improved orientation, stabilization and alignment of the spine.

Figure 7A:
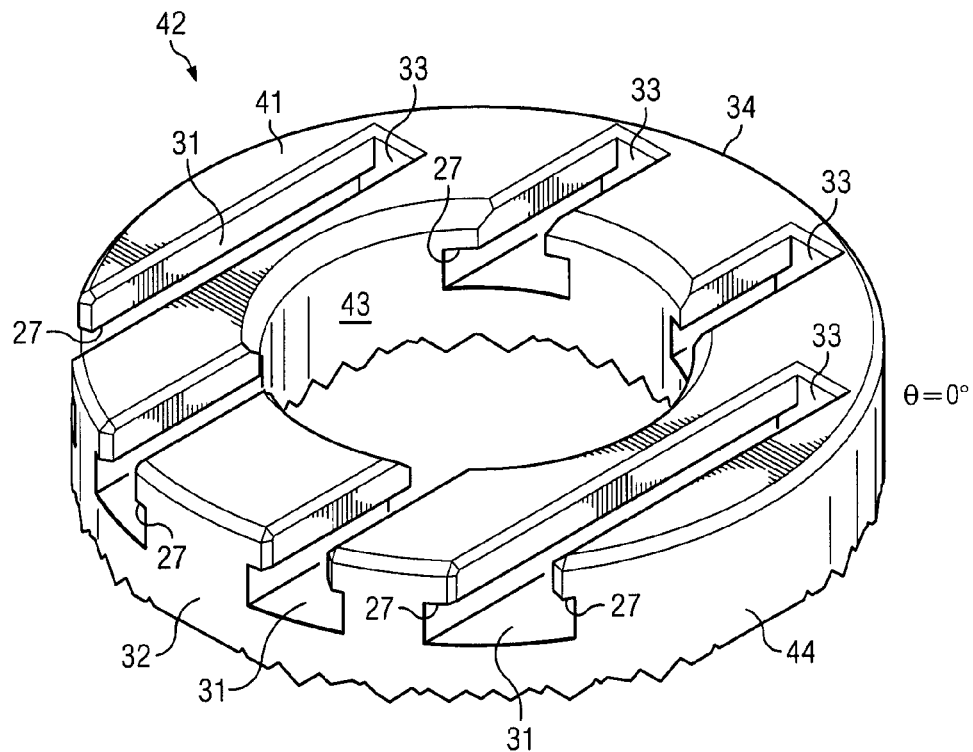
FIG. 7A is an isometric view of a zero degree end cap according to another embodiment.
Figure 7B:
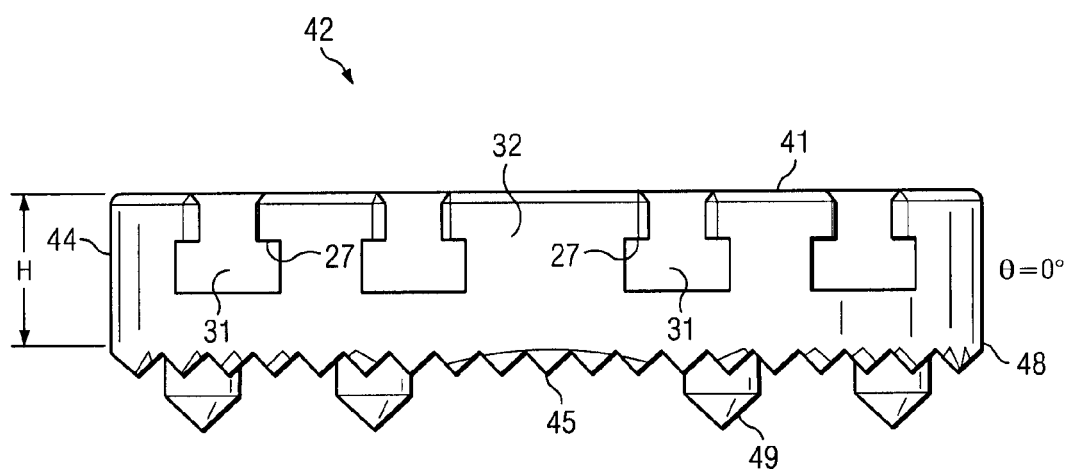
FIG. 7B is a side view of FIG. 7A.
Figure 8:
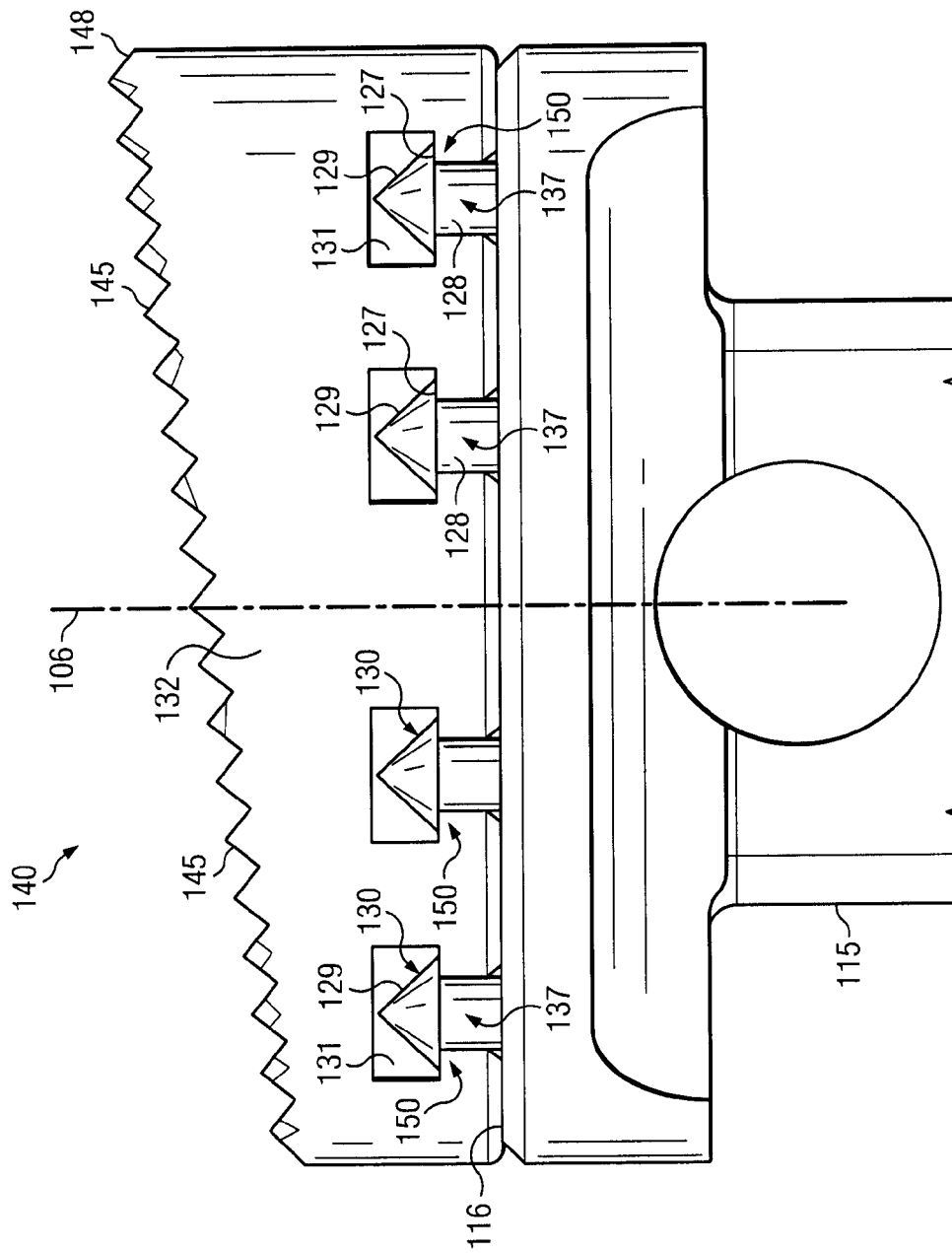
FIG. 8 is a section view of an implant base section and end cap according to another embodiment.

FIGS. 2, 3, 4A, 7A and 7B show an aspect where the lower end cap 42 angulation is zero degrees. In this aspect, the lower end cap 42 has an end cap height H that may take on a desired or required height value H but will not provide any implant angulation θ. The lower end cap 42 has an angulation θ of 0° degrees. Such an end cap 42 may be used where there is a need only for additional height to augment the implant 10 in the amount of an end cap height H as might be desired or required by a surgeon, medical procedure or clinical need. Such an end cap 42, having angulation θ of 0° degrees and a certain cap height H, as illustrated in FIGS. 2, 3 & 4A, is attached to the outer implant body 24. FIGS. 7A & 7B also illustrate such a zero degree end cap 42.

As previously discussed, the end cap 40 or 42 preferably comprises at least one positioning passage or end cap slot 31 which permits sliding insertion of positioning teeth 30 into one or more of the positioning passages or end cap slots 31 when the end cap 40 or 42 is positioned on the implant base section 15 and 25. The positioning passages or end cap slots 31 are preferably complementarily shaped and configured to permit the positioning teeth 30 to enter and slideably travel inside the end cap slots 31. The end cap slots 31 will have a size and configuration which complements the positioning teeth 30 and which permits sliding insertion of the positioning teeth 30 into the end cap slots 31. Those of skill in the art will recognize that different sizes, shapes and configuration may be used for the positioning passages or end cap slots 31 and complementary positioning teeth 30 depending on medical procedure or clinical need, or surgeon need or selection, as long as they permit sliding insertion of positioning teeth 30 into the end cap slots 31 when the end cap 40 or 42 is positioned on the implant base section 15 and 25.

As best shown in FIGS. 4A, 6C and 7B, the positioning passages or end cap slots 31 preferably extend from a first end cap end 32 across and towards an opposing second end cap end 34. The positioning passages or end cap slots 31 have an open end adjacent to the first end cap end 32 where the positioning teeth 30 will initially enter when the end cap is slideably inserted on the implant base section 15 and 25. The positioning passages or end cap slots 31 also preferably have end slot walls 33 at the opposing second end cap end 34 which will provide a travel end point for the positioning teeth 30 when the end cap 40 or 42 is slideably moved across the implant base section 15 and 25. In one preferred aspect, shown in FIGS. 2-4A and 5-7B, the positioning passages 31 are end cap slots 31 comprising a substantially T-shaped aperture configuration with slot shoulder walls 27 which will interact with the underside of the positioning teeth heads 29 to prevent axial movement of the end cap 40 or 42 relative to the implant base section 15 or 25. In an alternate embodiment, the positioning passages 31 do not have an end slot wall 33.

The positioning passages or end cap slots 31 are preferably located in the end cap 40 or 42 in an area between first end cap end 32 and opposing second end 34 of the end cap 40 or 42. In one aspect, the positioning passages or end cap slots 31 are substantially parallel to each other. The end cap 40 or 42 preferably has at least the same number of end cap slots 31 as the number of extending positioning teeth 30 which can align 37, so that the end cap 40 or 42 can be slideably inserted when the end cap 40 or 42 is moved onto the implant base section 15 and 25. In the aspect show in FIGS. 2-4A and 6A-7B, the positioning passages or end cap slots 31 are preferably spaced and located evenly or equidistantly across the end cap seating surface 41 in a substantially parallel configuration. The positioning teeth 30 are preferably located evenly or equidistantly around the periphery of the exterior surface 16 and 26, as best shown in FIGS. 4A and 4B, such that the positioning teeth align 37 to thereby permit sliding travel in a corresponding end cap slot 31. The spacing and location of the positioning passages or end cap slots 31 is configured to complementarily align with the sets of aligned 37 positioning teeth 30 to permit end cap 40 or 42 insertion and sliding positioning of the end cap 40 or 42 with the positioning teeth 30 of the implant base section 15 or 25. Those of skill in the art will recognize that the positioning passages or end cap slots 31 may also have other selected spacing and orientation in the end cap 40 or 42 as may be desired or required by a surgical procedure or clinical application, or surgeon need or selection. However, in such other selected spacing, the end cap slots 31 must still be spaced and located to complementarily align with the positioning teeth 30 to permit end cap 40 sliding insertion and positioning with the positioning teeth 30 of the implant base section 15 or 25.

The end cap 40 or 42 preferably has at least the same number of end cap slots 31 as the number of positioning teeth 30 sets which linearly align 37 so that the end cap 40 or 42 can be slideably inserted and positioned when the end cap 40 or 42 is positioned on the implant base section 15 and 25. This is the case since the positioning passages or end cap slots 31 accept entry of aligned 37 positioning teeth 30. For example, in the case shown in FIGS. 4A and 4B, the end cap 40 has four positioning passages or end cap slots 31 and the base section 15 has eight positioning base teeth 30 which align 37 into four sets of aligned positioning teeth 30. If there are two sets of aligned 37 positioning teeth 30, then the there must be at least two positioning passages or end cap slots 31. If there are four sets of aligned 37 positioning teeth 30, as is shown in FIGS. 4A and 4B, then there must be at least four end cap slots 31 in order that the end cap 40 can be inserted and slideably positioned on the implant base section 15. Those of skill in the art will recognize that the end cap 40 may also have more positioning passages or end cap slots 31 than sets of aligned 37 positioning teeth 30 which could provide a greater degree of control of placement of the end cap 40 on the implant base section.

In operation or use, the end cap slots 31 will engage and interlock with the plurality of corresponding and complementary positioning teeth 30 to form an end cap locking mechanism 50, shown in FIGS. 2, 3 & 5, with the end cap 40 or 42. The connection or locking mechanism 50 comprises positioning teeth 30 which engage and interlock with a plurality of corresponding and complementary positioning passages or end cap slots 31. As the end cap 40 or 42 travels over and across the exterior surface 16 or 26 of the implant base section 15 or 25, the positioning teeth 30 enter and engage the end cap slots 31 and thereafter slideably travel inside the end cap slots 31. The fit between the interlocking or engaging positioning teeth 30 and positioning passages or end cap slots 31 is preferably a friction fit sufficient to minimize or prevent movement between the positioning teeth 30 and positioning passages or end cap slots 31 once the end cap 40 or 42 is positioned at a desired end cap position on the first or second base section 15 or 25. The holding strength of the friction fit may be augmented or controlled by the addition or use of a coating substance between the end cap slots 31 and the positioning teeth 30. For example, a coating, such a silicone, may be used to increase friction between the end cap slots 31 and the positioning teeth 30. Those of skill in the art will recognize that other substances or friction control mechanism may be used to augment or control friction strength between the end cap slots 31 and the positioning teeth 30. Also, those of skill in the art will recognize that instead of a friction fit, other types of interlocking fit may be used, e.g., an interference fit, press fit, snap fit, etc. Further, as previously discussed, the complementary positioning teeth 30 and positioning passages or end cap slots 31 in the locking mechanism 50 cooperatively interact to prevent movement of the end cap 40 or 42 relative to the first or second base section 15 or 25 in an axial direction along the implant axis 5. Since the tooth head 29 is wider and larger than the tooth base 28, an attempt to axially move or remove the end cap 40 or 42 will result in the end cap slot shoulder walls 27 butting up against the underside of the tooth head 29 which thereby prevents the axial movement, and axial removal, of the end cap 40 or 42 from the first or second base section 15 or 25.

The complementary positioning passages or end cap slots 31 and positioning teeth 30, when lockingly engaged, result in a locking engagement sufficient to hold the end cap 40 or 42 on the implant base plate 15 or 25 to permit a surgeon to pre-assemble the end cap 40 or 42 to an implant 10 for insertion into an intervertebral disc space 101. Those of skill in the art will recognize that other sizes, shapes and configuration may be used for the positioning passages 31 and positioning teeth 30 depending on medical procedure or clinical need, or surgeon need or selection, as long as they have a complementary configurations which permits sliding insertion and positioning, and locking engagement of the end cap slots 31 and the positioning teeth 30 when the end cap 40 is positioned on the implant base section 15 and 25.

The end cap 40 is preferably selectively positioned or adjusted on the implant base section 15 or 25 through variation in the approach direction and orientation XY of the positioning passages or end cap slots 31 to the implant base section 15 and 25. The approach direction XY of the positioning passages 31 is selectively adjustable relative to the implant body 20 and implant base section 15 or 25 about the longitudinal axis 5 of the implant body 20. The approach direction XY of the positioning passages or end cap slots 31 determines the position at which the end cap 40 will be placed at or located on the implant base section 15 and 25. The more approach directions XY for the positioning passages or end cap slots 31 are available, the greater the degree of choice and control a surgeon will have in placing the end cap 40 or 42 on the implant base section 15 and 25 at a desired or final position or orientation. This aspect advantageously provides a surgeon selective control of where the end cap angulation $\theta$ and the end cap vertex height H will be positioned on the implant base section 15 or 25. The ability to selectively position the end cap angulation $\theta$ permits a surgeon to determine where the end cap angulation $\theta$ and end cap height H will be applied or imparted to an adjacent vertebral body 100 or 105. Prior to insertion of the implant 10 into the intervertebral disc space 101, the surgeon can decide where the end cap angulation $\theta$ and the end cap vertex height H are desired or needed for a particular medical procedure or clinical application. The surgeon can then select the appropriate approach direction XY for the positioning passages or end cap slots 31 to take so that the end cap 40 or 42 can be slideably positioned on the implant base section 15 or 25 to impart the desired end cap angulation $\theta$ and end cap height H to an adjacent vertebral body 100 or 105.

An appropriate approach direction XY is selected for the positioning passages or end cap slots 31 in order to selectively position the end cap 40 on the implant base plate 15 or 25. There will be a plurality of possible or available approach directions XY. The end cap slots 31 can then be slideably positioned and inserted onto the positioning teeth 30 of the implant base plate 15 or 25 at the desired or needed approach direction XY. As an illustration, FIG. 4B show two possible approach directions XY for the positioning passages or end cap slot 31. The availability of many approach directions XY enables selective positioning of the end cap angulation $\theta$ which in turn permits the surgeon to decide the point or location where the end cap angulation $\theta$ and end cap height H will be applied or imparted to an adjacent vertebral body 100 or 105. Having the ability to select the approach direction XY for the positioning passages or end cap slots 31 permits a surgeon to selectively vary or adjust the end cap's 40 angulation $\theta$ and the end cap vertex height H relative to the implant base section 15 so as to be able to position the end cap angulation $\theta$ and vertex height H at a desired or required point on the implant base section 15 or 25, the vertebral member 100 or 105 and/or vertebral disk space 101. For example at an anterior, antereolateral, posterior or lateral point about the vertebral member 100 or 105 or vertebral disk space 101. This is in turn will position the end cap angulation $\theta$ and vertex height H at a desired or required point relative to the adjacent intervertebral member 100 or 105 once the implant 10 is inserted and positioned within the intervertebral space 101. The end cap 40 will then be able to impart desired or required angulation $\theta$, orientation and vertex height H on the adjacent vertebral body 100 or 105 at selected or required points on the adjacent vertebral body 100 or 105 to correct or improve the angulation, orientation, alignment and stabilization of the spine or spinal anatomy.

The number of end cap slots 31 and corresponding aligned sets of positioning teeth 30 will impact the incremental degree of control, through the selectable end cap approach direction XY, that a surgeon will have in selecting the end cap angulation $\theta$ position between the implant 10 and the adjacent vertebral body 100 or 105. In one preferred aspect, shown in FIGS. 4A and 4B, the end cap 40 has four end cap slots 31 which correspond to pairs of aligned positioning teeth 30 which are evenly or equidistantly spaced on the implant base section 15. The positioning teeth 30 spacing permits eight alignment configurations 37 where the positioning teeth 30 can be paired up or aligned to permit the slideable positioning of the four positioning passages or end caps slots 31. FIG. 4A shows one alignment configuration 37 while FIG. 4B shows two alignment configurations 37. The eight possible discrete positioning teeth 30 alignment configurations 37 correspond to eight discrete and selectable approach directions XY for the end cap 40 and its four end cap slots 31. The eight discrete and selectable approach directions XY for the end cap 40 differ from each other by about forty-five degrees)(45° around the end cap 40 as shown in FIG. 4B. As such, the end cap 40 can be oriented, through appropriate selection of the approach direction XY, in single or multiple increments of forty-five degrees)(45° in order to set or select the end cap angulation $\theta$ position between the implant 10 and the adjacent vertebral body 100 or 105.

A greater degree of control for incrementally advancing the end cap 40 about the implant base section 15, through appropriate selection of the approach direction XY, may be obtained by increasing the number of end cap slots 31 and/or positioning teeth 30. For example, if the end cap 40 were to have five positioning passages or end cap slots 31 and the same number of eight positioning teeth 30. Then, the end cap 40 can be advanced, through appropriate selection of the approach direction XY, in single or multiple increments of thirty six degrees) (36° so as to position the end cap's angulation $\theta$ at different location points about the periphery of the adjacent vertebral body 100 or 105. In such a case, the end cap 40 can be selectively oriented to have a selective approach direction XY in order to position or reposition the end cap angulation $\theta$ point between the implant 10 and the adjacent vertebral body 100 or 105. The larger number of positioning passages or end cap slots 31, in this case, would provide a surgeon with the ability to position or reposition the end cap 40 in smaller discrete increments. This greater degree of control provides the surgeon with more precise control on where the end cap angulation θ will be positioned between the implant 10 and the adjacent vertebral body 100 or 105. In this manner, the selected angulation θ and end cap vertex height H can be imparted to an adjacent vertebral member 100 or 105 to thereby impart or drive angular orientation and height adjustment of the adjacent vertebral member 100 or 105 for correction or improved alignment, angulation, orientation, and stabilization of the spine or spinal anatomy.

Once the end cap 40 or 42 is preferably aligned and oriented, through selection of an appropriate or desired approach direction XY, the surgeon can insert and slideably move or force the end cap 40 or 42 onto the first and second base sections 15 and 25 so that the end cap 40 engages and locks onto the implant base plate 15 or 25, as shown in FIGS. 2, 3 & 5. The complementary and cooperating positioning teeth 30 and end cap slots 31 enable the end cap 40 or 42 to be slideably positioned on the implant base section 15 or 25. As discussed previously, the locking of the end cap 40 onto the implant base plate 15 or 25 is accomplished through the locking mechanism 50 where positioning teeth 30 and end cap slots 31 complementary interact and lockingly engage when the end cap 40 is positioned on the implant base section 15 and 25. The positioning teeth 30 can be referred to as male locking components and the end cap slots 31 can be female locking components.

FIG. 8 shows a section view of an implant base section 115 and end cap 140 being lockingly engaged according to another aspect of a locking mechanism 150. This aspect of the implant base section 115, end cap 140 and locking mechanism 150 have a similar operation and operation as the embodiment previously discussed. The implant base section 115 comprises a plurality of positioning teeth or spikes 130 which will accept and provide for slideable placement, positioning and engaging of the end cap 140 onto the implant base section 115. The positioning teeth 130 are configured to be inserted into and slideably travel inside the end cap 140 via corresponding and complementary configured positioning passages 131.

In this aspect, the positioning teeth 130 comprise a tooth head 129 and a tooth base 128 with a tooth base cutout 137. In this tooth base 128 configuration, the tooth head 129 extends laterally past the tooth base 128 over the tooth base cutout 137, as shown in FIG. 8. Those of skill in the art, will recognize that other positioning teeth 130 shapes or configurations may also be used, so long as the positioning teeth 130 can enter and slideably travel within the positioning passages or end cap slots 131 to permit the end cap 140 to be slideably positioned on the exterior surface 116 of the implant base section 115. The positioning teeth 130 enable the end cap 140 to be inserted into and slideably travel inside the end cap 140 or 42 via corresponding and complementary configured positioning passages or end cap slots 131. The positioning teeth 130 are also adapted to interlock and engage with the corresponding and complementary positioning passages 131 to form an end cap locking mechanism 150.

The positioning passages 131 are preferably end cap slots complementarily shaped and configured to permit the positioning teeth 130 to enter and slideably travel therein. In one aspect, the positioning passages or end cap slots 131 have an elongated aperture configuration with slot shoulder wall 127 which will interact with the tooth base cutout 137 at the underside of the positioning teeth heads 129. The positioning passages or end cap slots 131 extend from a first end 132 of the end cap 140 across and towards an opposing second end of the end cap 140. The positioning passages or end cap slots 131 are complementarily sized to permit the end cap teeth 130 to enter and slideably travel within the positioning passages 131 as the end cap 140 is moved across the base sections 115. The complementary positioning teeth 130 and end cap slots 131 enable the end cap 140 to be slid onto the first base section 115, and interact and engage the complementary positioning passages 131 to form the end cap locking mechanism 50.

FIG. 8 shows the locking mechanism 150 which in this aspect comprises positioning teeth 130 which engage and interlock with a plurality of corresponding and complementary positioning passages or end cap slots 131 to secure the end cap 140 to the first base sections 115. As the end cap 140 slideably travels over and across the exterior surface 116 of the implant base section 115, the positioning teeth 130 enter and engage the end cap slots 131 and thereafter slideably travel inside the end cap slots 131. The positioning teeth 130 and the end cap slots 131 have complementary shapes or configurations such that they cooperatively interact to lock or secure the end cap 140 onto the first base sections 115. The locking mechanism 150 permits the end cap 140 and the base section 115 to engage and interlock when the end cap 140 is slideably positioned on the base section 115. The fit between the interlocking or engaging positioning teeth 130 and end cap slots 131 is a friction fit sufficient to minimize or prevent movement between the positioning teeth 130 and end cap slots 131 once the end cap 140 is positioned at a desired end cap position on the first base section 115. Additionally, the positioning teeth 130 and complementary positioning passages 131 cooperatively engage and interact to prevent movement or travel of the end cap 140 in an axial direction along an implant axis 106 relative to the first base section 115. Since the tooth head 129 extends over and past the than the tooth base 128 at the tooth base cut out 137, an attempt to move or remove the end cap 140 in an axial direction will result in the end cap slot shoulder walls 127 butting up against the underside of the tooth head 129 at the tooth base cut out 137 thereby preventing axial movement or removal of the end cap 140 from the first or second base section 115.

FIG. 8 also shows an aspect where the end cap 140 has a contact surface 148 with only end cap knurls or teeth 45 extending from the end cap exterior surface 148 which can engage the end plates of an adjacent vertebral member. The end cap teeth 145 may be a series or pattern of uniform knurls or teeth 145 that cover the entire end cap exterior surface 148 or solely large spikes (not shown), or some combination, so long as they assist in providing a securing and stabilizing function of the combined end cap 140 and implant body.

The implants 10 and end caps 40, 42, and 140 may be implanted within a living patient for the treatment of various spinal disorders. The implant 10 may also be implanted in a non-living situation, such as within a cadaver, model, and the like. The non-living situation may be for one or more of testing, training, and demonstration purposes.

The end caps disclosed in this disclosure are preferably comprised of biocompatible materials substrates which can be used in combination with implants or devices configured to be inserted into an intervertebral space and contact against adjacent vertebral members. The biocompatible material substrate may include, among others, polyetheretherketone (PEEK) polymer material, homopolymers, co-polymers and oligomers of polyhydroxy acids, polyesters, polyorthoesters, polyanhydrides, polydioxanone, polydioxanediones, polyesteramides, polyaminoacids, polyamides, polycarbonates, polylactide, polyglycolide, tyrosine-derived polycarbonate, polyanhydride, polyorthoester, polyphosphazene, polyethylene, polyester, polyvinyl alcohol, polyacrylonitrile, polyamide, polytetrafluorethylene, poly-paraphenylene terephthalamide, polyetherketoneketone (PEKK); polyaryletherketones (PAEK), cellulose, carbon fiber reinforced composite, and mixtures thereof. The biocompatible material substrate may also be a metallic material and may include, among others, stainless steel, titanium, nitinol, platinum, tungsten, silver, palladium, cobalt chrome alloys, shape memory nitinol and mixtures thereof. The biocompatible material used can depend on the patient's need and physician requirements.

While embodiments of the invention have been illustrated and described in the present disclosure, the disclosure is to be considered as illustrative and not restrictive in character. The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An implant for insertion into an intervertebral space between a first and second vertebral member, the implant comprising:
   an implant body with at least one base section,
      the base section including two or more positioning teeth;
      and an end cap adapted for selective positioning at a selected point on the base section, the end cap comprising
         a seating surface adapted to contact the base section when the end cap is positioned on the implant body,
         an end cap angulation, and
         at least one end cap slot having a substantially T-shaped aperture adapted to receive the two or more positioning teeth, the substantially T-shaped aperture and positioning teeth complementarily configured to facilitate slideably positioning the end cap on the base section;
      wherein the implant imparts the end cap angulation to an adjacent vertebral body at the selected point when the implant is positioned in the intervertebral space.

2. The implant of claim 1, wherein the end cap is selectively positioned to the base section to prevent axial movement of the end cap relative to the base section.

3. The implant of claim 1, wherein the end cap is selectively positioned at the selected point on the base section via adjustment of an end cap approach direction.

4. The implant of claim 1, wherein the end cap angulation comprises an angular value selected from the'group of 0°, 4°, 8° and 15°.

5. The implant of claim 1, wherein the end cap angulation comprises an angular value in the range of between zero degrees to fifteen degrees) (0°-15°).

6. The implant of claim 1, wherein the end cap further comprises an end cap height measured relative to the seating surface which enables the implant to both impart end cap height and end cap angulation to the adjacent vertebral body at the selected point.

7. The implant of claim 1, wherein the base section is selectively positioned to the end cap through an interference fit, a compression fit, a friction fit or a press fit.

8. An implant for insertion into an intervertebral space between a first and second vertebral member, the implant comprising:
   an implant body with at least one base section,
      the base section including two or more aligned positioning teeth;
      an end cap adapted for selective positioning at a selected point on the base section, the end cap comprising
         a seating surface adapted to contact the base section when the end cap is positioned on the implant body,
         an end cap angulation,
         at least one end cap slot having a substantially T-shaped aperture adapted to slideably receive the aligned positioning teeth therein, the end cap slot and the two or more positioning teeth complementarily configured to facilitate slideably positioning the end cap on the base section;
      wherein the implant imparts the end cap angulation to an adjacent vertebral body at the selected point when the implant is positioned in the intervertebral space.

9. The implant of claim 8, wherein the end cap is selectively positioned to the base section to prevent axial movement of the end cap relative to base section.

10. The implant of claim 8, wherein the end cap is selectively positioned at the selected point on the base section via adjustment of an end cap approach direction.

11. The implant of claim 8, wherein the end cap angulation comprises an angular value in the range of between zero degrees to fifteen degrees) (0°-15°).

12. The implant of claim 8, wherein the end cap angulation comprises an angular value selected from the group consisting of 0°, 4°, 8° and 15°.

13. The implant of claim 8, wherein the end cap further comprises an end cap height measured relative to the seating surface which enables the implant to both impart end cap height and end cap angulation to the adjacent vertebral body at the selected point.

14. The implant of claim 10, wherein the base section is selectively positioned to the end cap through an interference fit, a compression fit, a friction fit or a press fit.

15. The implant of claim 1, wherein said end cap slot further comprises a slot shoulder wall.

16. The implant of claim 15, wherein said slot shoulder wall is configured to interact with an underside of the two or more positioning teeth to form a locking mechanism.

17. The implant of claim 1, wherein said end cap slot extends from a first end of the end cap toward an opposing second end of the end cap.

18. The implant of claim 8, wherein said end cap slot further comprises a slot shoulder wall.

19. The implant of claim 18, wherein said at least one slot shoulder wall is configured to interact with an underside of the two or more positioning teeth to form a locking mechanism.

20. The implant of claim 8, wherein said end cap slot extends from a first end of the end cap toward an opposing second end of the end cap.

* * * * *